United States Patent
Zhu et al.

(10) Patent No.: US 12,337,076 B2
(45) Date of Patent: Jun. 24, 2025

(54) APPLICATION OF NANO LAYERED DOUBLE HYDROXIDE IN CARTILAGE REGENERATION AND PREPARATION THEREOF

(71) Applicant: Tongji University, Shanghai (CN)

(72) Inventors: Rongrong Zhu, Shanghai (CN); Liming Cheng, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 18/822,374

(22) Filed: Sep. 2, 2024

(65) Prior Publication Data
US 2024/0416002 A1 Dec. 19, 2024

Related U.S. Application Data

(63) Continuation of application No. PCT/CN2023/094575, filed on May 16, 2023.

(30) Foreign Application Priority Data

May 16, 2022 (CN) .......................... 202210528029.1

(51) Int. Cl.
*A61L 27/04* (2006.01)
*A61L 27/38* (2006.01)

(52) U.S. Cl.
CPC ......... *A61L 27/047* (2013.01); *A61L 27/3834* (2013.01); *A61L 2400/12* (2013.01); *A61L 2430/06* (2013.01)

(58) Field of Classification Search
None
See application file for complete search history.

(56) References Cited

U.S. PATENT DOCUMENTS 11,357,888 B2 * 6/2022 Cheng .................. A61L 27/042

FOREIGN PATENT DOCUMENTS

| CN | 103966160 A | 8/2014 |
|----|-------------|--------|
| CN | 108339151 A | 7/2018 |

OTHER PUBLICATIONS

Kang et al. "Nanolayered hybrid mediates synergistic co-delivery of ligand and ligation activator for inducing stem cell differentiation and tissue healing" (2017), Biomaterials, 149: 12-28. (Year: 2017).*
Kuthati et al. "Layered double hydroxide nanoparticles for biomedical appliations: Current status and recent prospects" (2015), Applied Clay Science, 112-113: 10-116. (Year: 2015).*
Lee et al. "Layered Dobule Hydroxide and Polypeptide Thermogel Nanocomposite System for Chondrogenic Differentiation of Stem Cells" (2017), 9: 42668-42675. (Year: 2017).*
Wang et al. "Ion elemental-optimized layered double hydroxide nanoparticles promote chondrogenic differentiation and intervertebral disc regeneration of mesenchymal stem cells through focal adhesion signaling pathway" (2023), 22: 75-90. (Year: 2023).*
Wu et al. "Layered double hydroxide nanoparticles promote self-renewal of mouse embryonic stem cells through the PI3K signaling pathway" (2015), Nanoscale, 7: 11102-11114 (Year: 2015).*
Zhaojie Wang et al., "rBMSC osteogenic differentiation enhanced by graphene quantum dots loaded with immunomodulatory layered double hydroxide nanoparticles", Biomedical Materials, Jan. 14, 2022, pp. 1-12.
Li Yang et al., "Layered Double Hydroxide Nanoparticles with Osteogenic Effects as miRNA Carriers to Synergistically Promote Osteogenesis of MSCs", ACS Appl. Mater. Interfaces, Oct. 7, 2021, pp. 48386-48402.
CNIPA, Notification of First Office Action for CN202210528029.1, Apr. 27, 2023.
Tongji University (Applicant), Replacement claims (allowed) of CN202210528029.1, Oct. 9, 2023.
CNIPA, Notification to grant patent right for invention in CN202210528029.1, Oct. 18, 2023.

* cited by examiner

*Primary Examiner* — Teresa E Knight
(74) *Attorney, Agent, or Firm* — Hemisphere Law, PLLC; Zhigang Ma

(57) ABSTRACT

Application methods of a nano layered double include: applying the nano layered double hydroxide in promoting chondrogenic differentiation of human umbilical cord-derived mesenchymal stem cells, and applying the nano layered double hydroxide in preparing drugs for promoting cartilage regeneration, promoting intervertebral disc repair, or treating intervertebral disc degeneration. Compared to human umbilical cord-derived mesenchymal stem cells without an addition of the nano layered double hydroxide, the human umbilical cord-derived mesenchymal stem cells with the addition of the nano layered double hydroxide have a better and faster ability to differentiate into chondrocytes and broad application prospects.

2 Claims, 4 Drawing Sheets
Specification includes a Sequence Listing.

APPLICATION OF NANO LAYERED DOUBLE HYDROXIDE IN CARTILAGE REGENERATION AND PREPARATION THEREOF

CROSS-REFERENCE TO RELATED APPLICATIONS

This application is a continuation of International Patent Application No. PCT/CN2023/094575, filed May 16, 2023, which claims the priority of Chinese Patent Application No. 202210528029.1, filed May 16, 2022, both of which are herein incorporated by reference in their entirety.

TECHNICAL FIELD

The disclosure relates to the field of induced differentiation of stem cells, and more particularly to an application of a nano layered double hydroxide (LDH) in cartilage regeneration and preparation thereof.

STATEMENT REGARDING SEQUENCE LISTING

The sequence listing associated with this application is provided in text format in lieu of a paper copy and is hereby incorporated by reference into the specification. The name of the XML file containing the sequence listing is 24054THXT-USP1-US-2024-0057-SL.xml. The XML file is 15,173 bytes; is created on Aug. 19, 2024; and is being submitted electronically via patent center.

BACKGROUND

Degenerative disc disease is an age-related disease that occurs when one or more intervertebral discs between spine vertebrae degenerate or rupture, leading to lower back pain. The lower back pain is a third leading cause of disability in developed countries. The intervertebral disc is a complex avascular connective tissue cartilage structure, and a peripheral structure of the intervertebral disc is composed of a thick outer ring of fibrocartilage called annulus fibrosus. Mesenchymal stem cells have good proliferative capacity and multilineage differentiation potential, along with strong self-renewal abilities, providing a promising regenerative therapeutic alternative for a treatment of disc degeneration. Biomaterials play an indispensable role in cartilage tissue engineering, and by degradable materials with an optimized design to deliver cytokines, seed cells can be stimulated to adhere, proliferate, and differentiate, thereby promoting intervertebral disc regeneration. Therefore, constructing ideal materials that promote differentiation of the mesenchymal stem cells into cartilage is crucial for reconstruction and regeneration of the intervertebral discs.

Nano layered double hydroxides (LDHs) are inorganic nanomaterials with a layered structure formed by organically combining divalent metal hydroxides and trivalent metal hydroxides. The nano LDHs exhibit many potential applications in the field of biomedicine. For instance, a Chinese Patent Application No. 201810126426.X (with publication No. CN108339151A) previously filed by the applicant discloses that a nano inorganic LDH-neurotrophic factor 3 has a significant restorative effect on behavior of mice with transected and aspirated spinal cord injury models, showing significant recovery in electrophysiological behavior of the mouse models, and over time, electrophysiological signals are enhanced, indicating that neural circuits in an injured area can be reconstructed. A Chinese Patent Application with publication No. CN103966160A discloses that without the addition of leukemia inhibitory factors (LIFs), nano LDHs can promote expressions of various pluripotency genes in mouse embryonic stem cells and inhibit cell differentiation, and treated cells still have potential to differentiate into all three germ layers.

However, there are currently no reports on inducing chondrogenic differentiation of human mesenchymal stem cells by the nano LDHs.

SUMMARY

In response to problem in the related art, the disclosure aims at providing an application of a nano LDH in cartilage regeneration and a preparation of the nano LDH. Specific technical solutions are as follows.

In a first aspect, the disclosure provides an application method, including: applying the nano LDH in promoting chondrogenic differentiation of mesenchymal stem cells.

In an embodiment, the mesenchymal stem cells are umbilical cord-derived mesenchymal stem cells.

In an embodiment, furthermore, the mesenchymal stem cells are human umbilical cord-derived mesenchymal stem cells.

In a second aspect, the disclosure provides an application method, including: applying the nano LDH in preparing drugs for promoting cartilage regeneration, promoting intervertebral disc repair, or treating intervertebral disc degeneration.

In the above application methods, the general formula of the nano LDH is $[M^{2+}_{(1-x)}M^{3+}_{x}(OH)_2]_{x+}[A^{n-}]_{x/n}\cdot zH_2O$, the $M^{2+}$ represents divalent metal cation, the $M^{3+}$ represents a trivalent metal cation, $A^{n-}$ represents an anion with an interlayer valence of n, x represents a molar ratio of trivalent cations to all cations, and z represents the number of crystal water molecules per nano LDH molecule. Salts formed by $M^{2+}$ and $M^{3+}$ are soluble or slightly soluble.

In an embodiment, the $M^{2+}$ is magnesium ion ($Mg^{2+}$), zinc ion ($Zn^{2+}$) or calcium ion ($Ca^{2+}$).

In an embodiment, the $M^{3+}$ is aluminum ion ($Al^{3+}$) or ferric ion ($Fe^{3+}$).

In an embodiment, the $A^{n-}$ is chloride ion ($Cl^-$), nitrate ion ($NO_3^-$) or sulfate ion ($SO_4^{2-}$).

In an embodiment, $(1-x):x=(0.1-5):1$.

In a third aspect, the disclosure provides a liquid formulation for promoting the chondrogenic differentiation of the mesenchymal stem cells, promoting the cartilage regeneration, promoting the intervertebral disc repair, or treating the intervertebral disc degeneration. The liquid formulation includes mesenchymal stem cells and the nano LDH.

In an embodiment, a concentration of the nano LDH in the liquid formulation is in a range of 1 microgram per milliliter (µg/mL) to 40 µg/mL.

In an embodiment, the mesenchymal stem cells in the liquid formulation are umbilical cord-derived mesenchymal stem cells.

In an embodiment, the mesenchymal stem cells in the liquid formulation are human umbilical cord-derived mesenchymal stem cells.

In a fourth aspect, the disclosure provides a preparation method of the nano LDH, including the following steps:
(1) dissolving a soluble divalent metal ion salt and a soluble trivalent metal ion salt in water to prepare a metal ion salt solution;

(2) preparing a sodium hydroxide (NaOH) solution by using a double-distilled water (ddH$_2$O) with carbon dioxide (CO$_2$) removed as a solvent;

(3) adding the metal ion salt solution to the NaOH solution with vigorous stirring, under a nitrogen (N$_2$) atmosphere, to obtain a first suspension;

(4) transferring the first suspension to a hydrothermal synthesis reactor and then heating the first suspension at 80-120 degrees Celsius (° C.) for 14-18 hours (h) to obtain a second suspension; and (5) centrifuging the second suspension to obtain a product, washing the product by ddH$_2$O with CO$_2$ removed followed by drying to obtain the nano LDH.

In an embodiment, the divalent metal ion of the soluble divalent metal ion salt is any one of the Mg$^{2+}$, the Zn$^{2+}$ and the Ca$^{2+}$.

In an embodiment, the trivalent metal ion of the soluble trivalent metal ion salt is the Al$^{3+}$ or the Fe$^{3+}$.

In an embodiment, the soluble divalent metal ion salt includes any one selected from the group consisting of magnesium nitrate (Mg(NO$_3$)$_2$), zinc nitrate (Zn(NO$_3$)$_2$), calcium nitrate (Ca(NO$_3$)$_2$), magnesium chloride (MgCl$_2$), zinc chloride (ZnCl$_2$), calcium chloride (CaCl$_2$), magnesium sulfate (MgSO$_4$), zinc sulfate (ZnSO$_4$), and calcium sulfate (CaSO$_4$).

In an embodiment, the soluble trivalent metal ion salt includes any one selected from the group consisting of aluminum nitrate (Al(NO$_3$)$_3$), ferric nitrate (Fe(NO$_3$)$_3$), ferric chloride (FeCl$_3$), aluminum chloride (AlCl$_3$), aluminum sulfate (Al$_2$(SO$_4$)$_3$), and ferric sulfate (Fe$_2$(SO$_4$)$_3$).

In an embodiment, a mole ratio of the divalent metal ion to the trivalent metal ion is (0.1-5):1.

In an embodiment, a concentration of the NaOH solution in the step (2) is in a range of 0.015-0.05 moles per liter (M).

In an embodiment, a vigorous stirring speed in the step (3) is in a range of 400-2000 revolutions per minute (rpm).

In an embodiment, the drying in the step (5) is vacuum drying.

The disclosure has beneficial effects as follows.

In the disclosure, the nano LDH is first used to promote the chondrogenic differentiation of the human umbilical cord-derived mesenchymal stem cells (hUCMSCs). It can be seen, from experiments on cell viability detection, observations of Alcian Blue staining, and real-time quantitative polymerase chain reaction (PCR) detection of expressions of cartilage differentiation genes, that the nano LDH has good compatibility with cells and low cytotoxicity. Compared with hUCMSCs without an addition of the nano LDH, the hUCMSCs with the addition of the nano LDH have a better and faster ability to differentiate into chondrocytes, and also have higher expression of seven pluripotency marker genes associated with chondrogenic differentiation: SRY-box transcription factor 9 (SOX 9), collagen type X (COLX), collagen type I alpha 1 chain (COL1A1), collagen type III alpha 1 chain (COL3A1), COL3A1-2, collagen type VI alpha 1 chain (COL6A1), and mohawk homeobox (MKX). After processing the hUCMSC with the nano LDH and transplanting the processed hUCMSC into a rat intervertebral disc degeneration model caused by needle puncture, the degenerated intervertebral discs can be repaired. Therefore, the nano LDH has an advantage of promoting the chondrogenic differentiation of the hUCMSC and has broad application prospects.

DETAILED DESCRIPTION OF EMBODIMENTS

The specific embodiments provided by the disclosure are described below in detail with reference to the accompanying drawings.

The hUCMSCs are a type of stem cells with low immunogenicity, capable of self-renewal, proliferation, and multilineage differentiation capabilities. The hUCMSCs can differentiate into bone, cartilage, fat, and nerve cells. The hUCMSCs also have advantages of wide sources, strong plasticity, no adverse effects on donors and no ethical restrictions, and have the ability to secrete cytokines. Therefore, the hUCMSCs, as seed cells in cartilage regeneration and cartilage development, are used in experimental research, which has advantages of short experimental cycle and easy differentiation induction, and are conducive to experiment standardization. Therefore, the disclosure mainly uses the hUCMSCs as the seed cells.

In the following embodiments, Dulbecco's modified eagle medium/nutrient mixture F-12 (DMEM/F12), fetal bovine serum (FBS), non-essential amino acids, glutamine, and double antibiotics are essential components of a cell culture medium, used to maintain normal cell growth and commercially available products purchased from Gibco, USA. Other non-self-made reagents and raw materials are general commercial products available on the market.

In the following embodiments, nano LDH is prepared by variations of elemental ratio and compositions including various metal ions and anions, and hUCMSCs treated with various nano LDHs are induced to differentiate into cartilage. Experimental results show that the various nano LDHs promote chondrogenic differentiation of the hUCMSCs to varying degrees. The most effective synthesis method is demonstrated in embodiment 1, while other types of materials are shown in embodiments 2-4.

Embodiment 1

A nano LDH is prepared by following steps 1-6.

Step 1, 60 mL salt solution is prepared by using 6 millimoles (mmol) Mg(NO$_3$)$_2$ and 2 mmol Fe(NO$_3$)$_3$; a mole ratio of Mg$^{2+}$ to Fe$^{3+}$ is 3:1.

Step 2, 40 mL of 0.016 M NaOH solution is prepared by using ddH$_2$O with CO$_2$ removed as a solvent.

Step 3, the 60 mL salt solution in the step 1 is added to the 40 mL of 0.016 M NaOH solution in the step 2 with vigorous stirring (with a speed of 400 rpm), while continuously supplying $N_2$, to obtain a first suspension.

Step 4, the first suspension is transferred to a hydrothermal synthesis reactor and then heated at 100° C. for 18 hours to obtain a second suspension.

Step 5, the second suspension is centrifuged at 20000 gravitational accelerations (g) for 15 minutes (min) to obtain a product, the product is washed twice by dd$H_2$O with $CO_2$ removed to obtain a gel-like material, and the gel-like material is stored in a refrigerator at 4° C.

Step 6, the gel-like material in the step 5 is dried in a vacuum drying oven to obtain the nano LDH. The nano LDH is observed by a transmission electron microscopy.

Figure 1:
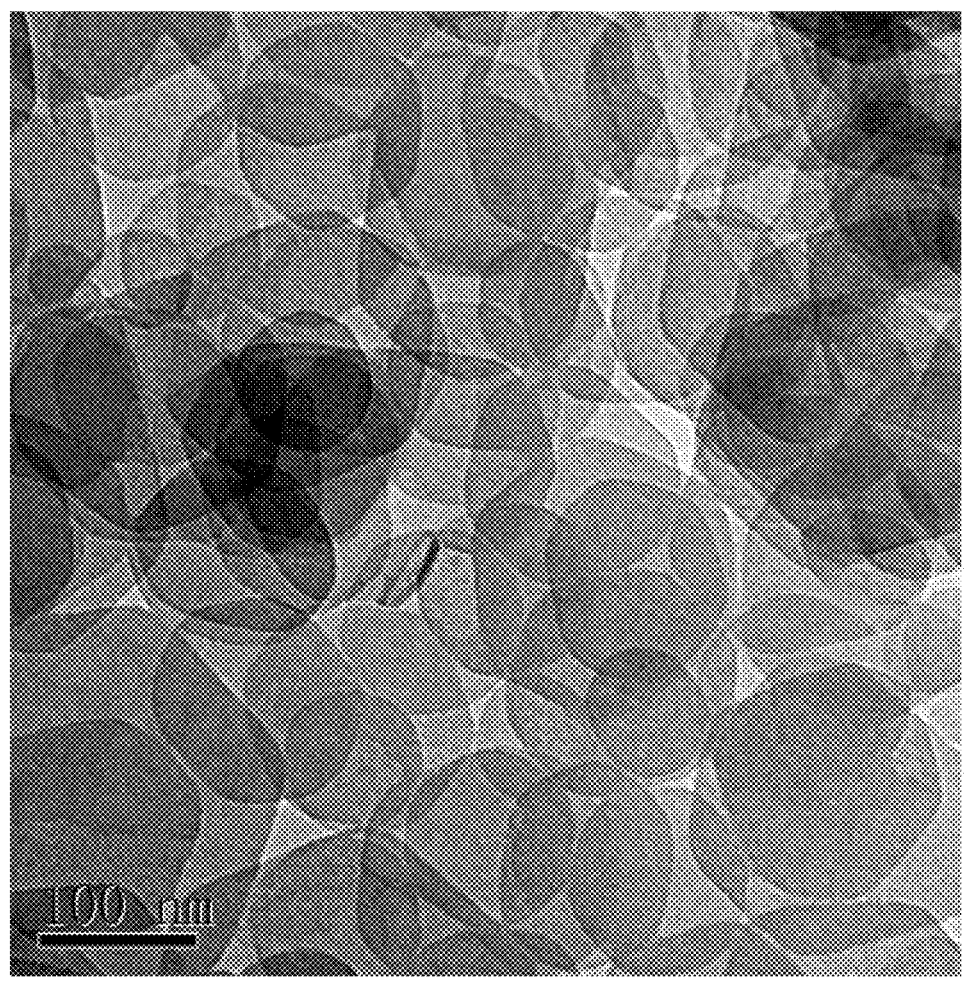
FIG. 1 illustrates a transmission electron microscopy image of a nano LDH according to an embodiment 1 of the disclosure.

FIG. 1 illustrates a transmission electron microscopy image of the nano LDH in the embodiment 1 of the disclosure. As shown in FIG. 1, the nano LDH has a good crystal structure with a hexagonal shape, and is relatively evenly distributed with a particle size of 100-120 nanometers (nm).

Embodiment 2

The difference between the embodiment 1 and embodiment 2 is that in the step 1, the $Mg(NO_3)_2$ is replaced with $Zn(NO_3)_2$, and $Fe(NO_3)_3$ is replaced with $Al(NO_3)_3$, and a molar ratio of $Zn^{2+}$ to $Al^{3+}$ in a prepared metal ion salt solution is 0.1:1. The rest operations are the same as in the embodiment 1 to ultimately obtain a nano LDH.

Embodiment 3

The difference between the embodiment 1 and embodiment 3 is that in the step 1, the $Mg(NO_3)_2$ is replaced with $MgCl_3$, and $Fe(NO_3)_3$ is replaced with $FeCl_3$ and a molar ratio of $Mg^{2+}$ to $Fe^{3+}$ in a prepared metal ion salt solution is 1:1. The rest operations of the embodiment 3 are the same as in the embodiment 1 to ultimately obtain a nano LDH.

Embodiment 4

The difference between the embodiment 1 and embodiment 4 is that in the step 1, the $Mg(NO_3)_2$ is replaced with $CaSO_4$, and $Fe(NO_3)_3$ is replaced with $Fe_2(SO_4)_3$ and a molar ratio of $Ca^{2+}$ to $Fe^{3+}$ in a prepared metal ion salt solution is 5:1. The rest operations of the embodiment 4 are the same as in the embodiment 1 to ultimately obtain a nano LDH.

Embodiment 5

1. Cell Viability Test (CCK-8 Method)
Step 1, hUCMSC culture.

The hUCMSCs are inoculated to a 96-well plate at a density of 8000 cells/well, and then cultured in a hUCMSC culture medium at 37° C. and 5% $CO_2$ for 18-24 h to obtain first cultured hUCMSCs for subsequent drug or material treatment. The hUCMSC culture medium includes: the DMEM/F12, the FBS and the double antibiotics. In this experiment, the culture time is 24 hours.

Step 2, six different concentrations of nano LDH solutions are prepared with concentrations of 1 μg/mL, 2.5 μg/mL, 5 μg/mL, 10 μg/mL, 20 μg/mL and 40 μg/mL, respectively.

Figure 2:
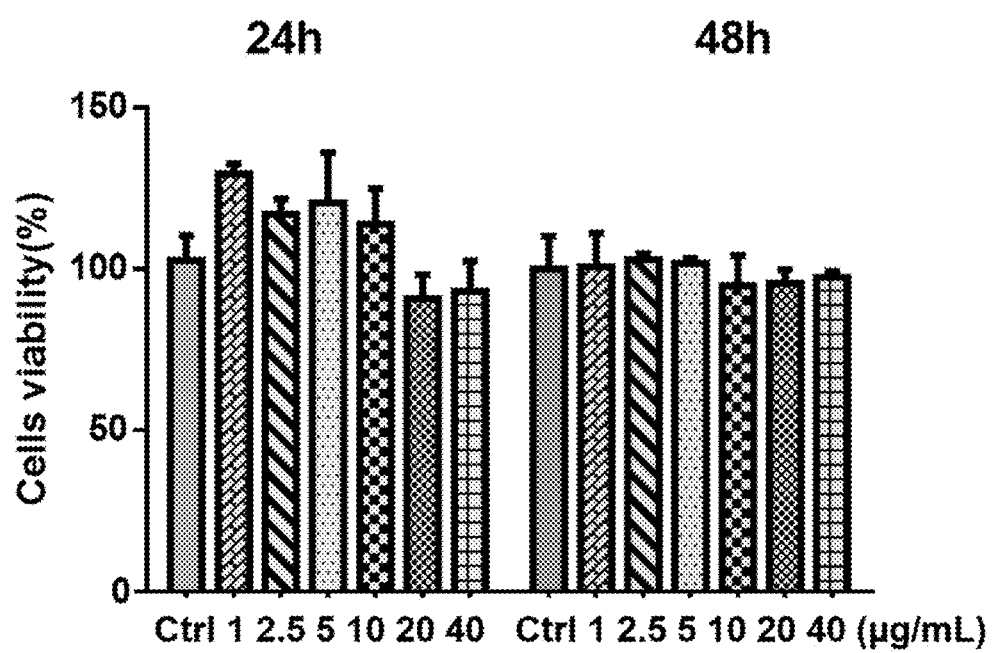
FIG. 2 illustrates cytotoxicity results of hUCMSCs treated with different concentrations of the nano LDH in the embodiment 1 for 24 h and 48 h by a cell counting kit-8 method (CCK-8); where an x-axis represents the concentration of the nano LDH, and a y-axis represents a cell viability rate of the hUCMSCs, with the cell viability rate of a blank control group set at 100%.

Step 3, supernatant is removed from the first cultured hUCMSCs, each well of the 96-well plate is added with one of the six different concentrations of the nano LDH solutions prepared in the step 2 respectively, after culturing for 24 h and 72 h, each well is added with 10 microliters (L) of CCK-8 solution at a concentration of 5 milligrams per milliliter (mg/mL) and then placed in the dark for 2 h, followed by shaking the 96-well plate in the dark for 10 seconds (s), then, an optical density (OD) value at 455 nm of each well is observed by a microplate reader, as shown in FIG. 2.

FIG. 2 illustrates cytotoxicity results (the CCK-8 method) of the hUCMSCs treated with different concentrations of the nano LDH in the embodiment 1 for 24 h and 48 h; where an x-axis represents the concentration of the nano LDH, and a y-axis represents a cell viability rate of the hUCMSCs, with the viability rate of a blank control group set at 100%. As shown in FIG. 2, when the nano LDH concentrations are 1 μg/mL, 2.5 μg/mL, 5 μg/mL, 10 μg/mL, 20 μg/mL and 40 μg/mL, respectively, after treating the hUCMSCs for 24 h and 48 h, the cell viability rates of the hUCMSCs treated with the different concentrations of the nano LDH show no significant difference compared to the blank control group.

2. Alcian Blue Staining.

The hUCMSCs are inoculated to a 24-well plate at a density of $2.5 \times 10^4$ cells/mL, and then cultured in an incubator at 5% $CO_2$ and 37° C. for 24 h until a cell confluence reaches 70% to obtain second cultured hUCMSCs. Nano LDH solutions are prepared by the hUCMSC culture medium at concentrations of 5 μg/mL, 10 μg/mL, 20 μg/mL and 40 μg/mL, respectively. After treating the second cultured hUCMSCs with the nano LDH solutions for 10 days, 14 days and 21 days, cells on the 24-well plate are fixed by 4% paraformaldehyde (FPA) at room temperature for 30 min to obtain a cell-fixed plate, the 4% FPA is removed from the cell-fixed plate followed by washing the cell-fixed plate twice by 1×phosphate-buffered saline (PBS) to obtain a first washed plate, the first washed plate is added with an Alcian blue staining solution for staining 30 min to obtain a stained plate, the Alcian blue staining solution is removed from the stained plate followed by washing the stained plate twice by 1×PBS to obtain a second washed plate. The second washed plate is placed under a microscope to observe a chondrogenic staining effect based on cell morphology and staining intensity.

Figure 3:
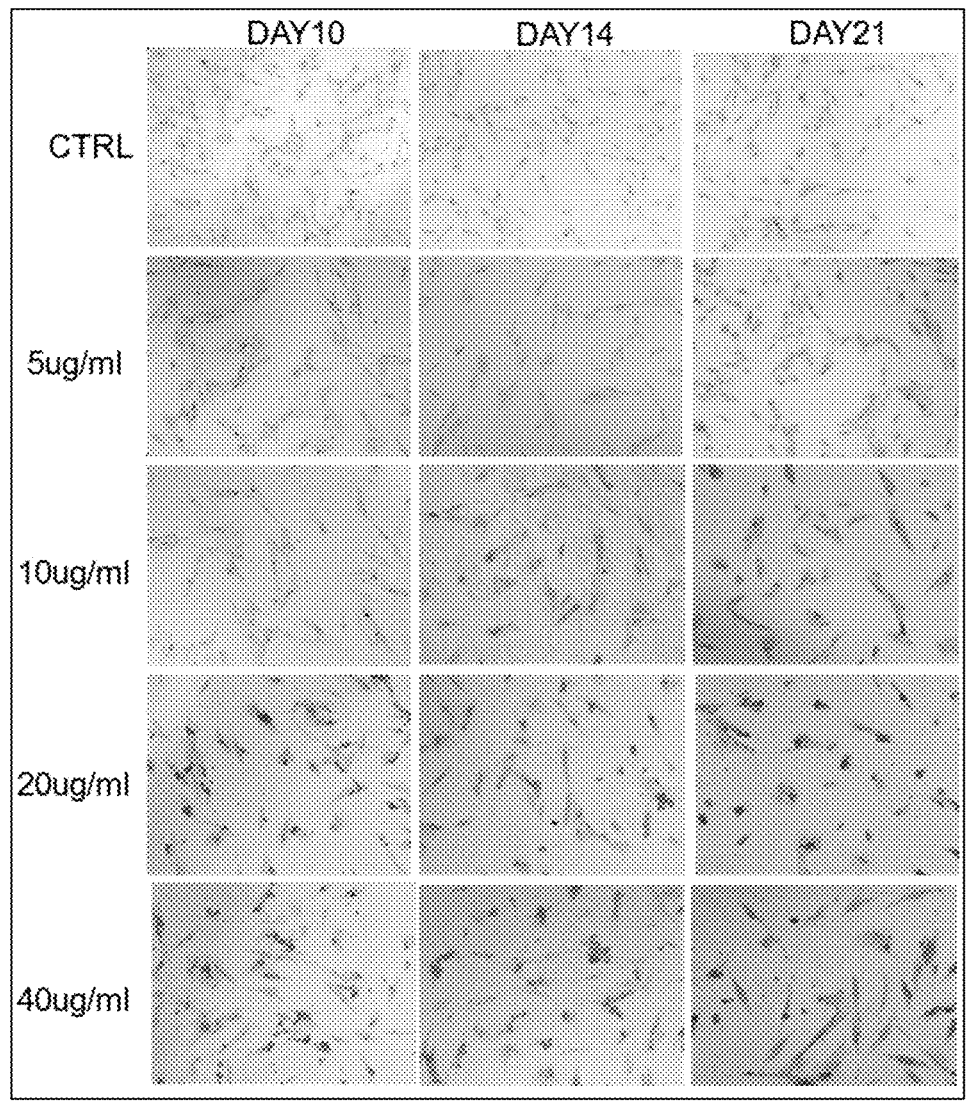
FIG. 3 illustrates an Alizarin blue staining image of the hUCMSCs treated with the different concentrations of the nano LDH in the embodiment 1 of the disclosure for 10 days, 14 days, and 21 days.

FIG. 3 illustrates an Alizarin blue staining image of the hUCMSCs treated with the different concentrations of the nano LDH in the embodiment 1 of the disclosure for 10 days, 14 days, and 21 days. As shown in FIG. 3, compared to untreated cells, the morphology of the hUCMSCs treated with the nano LDH gradually differentiated towards chondrocyte-like cells. Moreover, the intensity of the blue stain deepened with prolongation of treatment time, indicating that hUCMSCs are differentiating into chondrocytes under the differentiation-promoting effect of the nano LDH.

3. Real-Time Quantitative PCR Detection of Chondrogenic Gene Expression

The hUCMSCs are inoculated to a 6-well plate at a density of $5 \times 10^4$ cells/mL, and then cultured in an incubator with 5% $CO_2$ at 37° C. for 24 h until a cell confluence reaches 70% to obtain third cultured hUCMSCs. A nano LDH solution is prepared by the hUCMSC culture medium at a concentration of 10 μg/mL. After treating the third cultured hUCMSCs with the nano LDH solution for 10 days and 14 days, real-time quantitative PCR is used to detect changes in expression levels of cartilage-related genes such as SOX9 and COLX in the treated hUCMSCs, with glyceraldehyde-3-phosphate dehydrogenase (Gapdh) set as the reference gene. Specific primer sequences are as follows: Gapdh, forward primer: CTCCTCACAGTTGCCATGTA (SEQ ID NO: 1), reverse primer: GTT-GAGCACAGGGTACTTTATTG (SEQ ID NO: 2); SOX9, forward primer: ACCTTTGGGCTGCCTTATATT (SEQ ID NO: 3), reverse primer: TCCCTCACTCCAAGAGAAGAT (SEQ ID NO: 4); COLX, forward primer: ACC-CAAGGACTGGAATCTTTAC (SEQ ID NO: 5), reverse primer: GCCATTCTTATACAGGCCTAC (SEQ ID NO: 6); collagen type II alpha 1 chain (COL2), forward primer: AGGAGGCTGGCAGCTGTGTGC (SEQ ID NO: 7), reverse primer: CACTGGCAGTGGCGAGGTCAG (SEQ ID NO: 8); cartilage oligomeric matrix protein (COMP), forward primer: AAGAACGACGACCAAAAGGAC (SEQ ID NO: 9), reverse primer: CATCCCCTATACCATCGCCA (SEQ ID NO: 10); tenomodulin (TNMD), forward primer: CCATGCTGGATGAGAGAGGTT (SEQ ID NO: 11), reverse primer: TTGGTAGCAGTATGGATATGGGT (SEQ ID NO: 12); MKX, forward primer: CGAACAACTACCAT-GATGGGAAA (SEQ ID NO: 13), reverse primer: TTCT-GATGACGATGGAGACACTA (SEQ ID NO: 14); aggrecan (ACAN), forward primer: AGTCCTCAAGCCTCCTGTACTCA (SEQ ID NO: 15), reverse primer: GCAGTTGATTCTGATTCACGTTTC (SEQ ID NO: 16).

Figure 4:
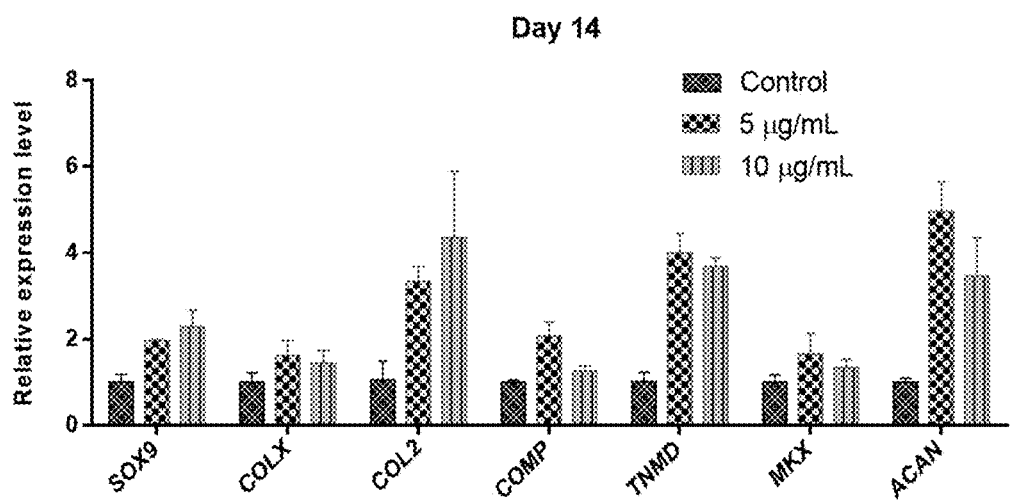
FIG. 4 illustrates an expression level bar chart of seven pluripotency genes when hUCMSCs are treated with 10 µg/mL of the nano LDH in the embodiment 1 of the disclosure for 14 days; where an x-axis represents different chondrocyte marker genes, and a y-axis represents relative expression levels of genes, with the relative expression level of a control group set at 1.

FIG. 4 illustrates an expression level bar chart of cartilage differentiation genes SOX9, COLX, COL2, COMP, TNMD, MKX and ACAN, when the hUCMSCs are treated with 5 g/mL and 10 µg/mL of the nano LDH in the embodiment 1 of the disclosure respectively for 14 days; where an x-axis represents different chondrocyte marker genes, and a y-axis represents relative expression levels of genes, with the relative expression level of a control group set at 1. As can be seen from FIG. 4, after co-culturing with a certain concentration of the nano LDH for 14 days, the expression levels of cartilage cell marker genes SOX9, COLX, COL2, COMP, TNMD, MKX, and ACAN all increased to varying degrees, indicating that the hUCMSCs differentiate into cartilage cells under the induction of the nano LDH.

4. X-Ray and MRI Detection of the Recovery Effect of Rat Intervertebral Discs after Acupuncture Transplanted with hUCMSCs Treated with the Nano LDH.

The hUCMSCs are inoculated into a 10-centimeter (cm) culture dish at a cell density of $2.5 \times 10^4$ cells/mL, and then cultured in an incubator at 5% $CO_2$ and 37° C. for 24 h until a confluence density reaches 70% to obtain fourth cultured hUCMSCs. A nano LDH solution is prepared using the hUCMSC culture medium, with a concentration set at 10 µg/mL, and the fourth cultured hUCMSCs are treated with the nano LDH solution for 7 days for later use. Eight-week-old male rats are selected to prepare an intervertebral disc degeneration model, with a modeling location at coccygeal vertebrae of each rat. A 21-gauge (G) skin puncture needle is inserted from one side of the intervertebral disc annulus fibrosus for 5 mm, rotated 360° and then maintained for 30 s before being withdrawn. Then, the hUCMSCs treated with the nano LDH are transplanted with a cell transplant volume of $1 \times 10^6$ per rat, and a control group is injected with an equal amount of culture medium. X-ray detection is performed after transplantation for 4 weeks and 8 weeks, and MRI detection is performed after transplantation for 8 weeks and 12 weeks.

Figure 5:
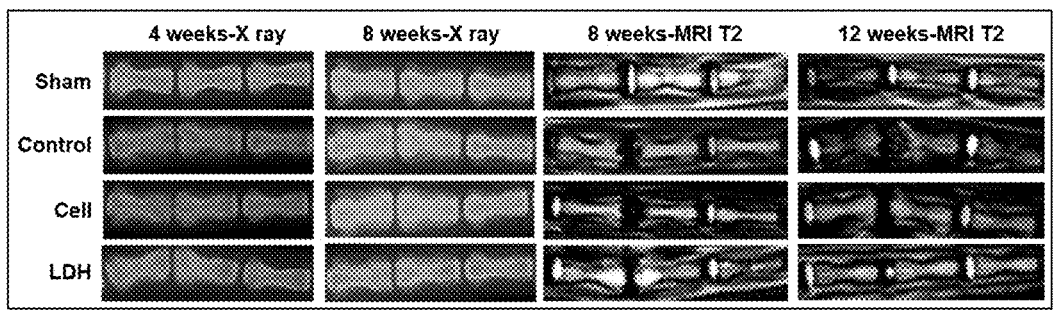
FIG. 5 illustrates an X-ray and magnetic resonance imaging (MRI) image of rat intervertebral discs after needle puncture transplanted into the hUCMSCs treated with the nano LDH.

FIG. 5 illustrates an X-ray and MRI image of the rat intervertebral discs after needle puncture transplanted into the hUCMSCs treated with the nano LDH. As time progresses, the X-ray results show that the LDH-treated hUCMSC transplant group (i.e., the LDH group) can better restore an intervertebral height of a degenerated intervertebral disc, and the MRI results show that the hUCMSCs treated with the nano LDH transplant group can better restore the tissue structure of the intervertebral disc.

The above descriptions are only the preferred embodiments of the disclosure. It should be noted that for those skilled in the art, without deviating from the method of the disclosure, multiple improvements and supplements can also be made. The improvements and supplements should also be considered within the scope of protection of the disclosure.

What is claimed is:

1. A method for preparing a nano layered double hydroxide (LDH), comprising:
step 1, preparing 60 milliliters (mL) salt solution by using 6 millimoles (mmol) magnesium nitrate and 2 mmol ferric nitrate, wherein a mole ratio of magnesium ion to ferric ion is 3:1;
step 2, preparing 40 ml of 0.016 moles per liter (M) sodium hydroxide solution by using double-distilled water with carbon dioxide removed as a solvent;
step 3, adding the 60 mL salt solution of step 1 to the 40 ml of 0.016 M sodium hydroxide solution of step 2 with stirring while continuously supplying nitrogen gas to obtain a first suspension;
step 4, transferring the first suspension to a hydrothermal synthesis reactor and then heating the first suspension at 100 degrees Celsius (C) for 18 hours to obtain a second suspension;
step 5, centrifuging the second suspension at 20000 gravitational accelerations (g) for 15 minutes (min) to obtain a product, washing the product twice with double-distilled water with carbon dioxide removed to obtain a gel-like material, and storing the gel-like material in a refrigerator at 4° C.; and
step 6, drying the gel-like material of step 5 in a vacuum drying oven to obtain the nano LDH; and
wherein the nano LDH is used to promote chondrogenic differentiation of human umbilical cord-derived mesenchymal stem cells.

2. A method for preparing a nano LDH, comprising:
step 1, preparing 60 mL salt solution by using 6 millimoles (mmol) magnesium nitrate and 2 mmol ferric nitrate, wherein a mole ratio of magnesium ion to ferric ion is 3:1;
step 2, preparing 40 ml of 0.016 moles per liter (M) sodium hydroxide solution by using double-distilled water with carbon dioxide removed as a solvent;
step 3, adding the 60 mL salt solution of step 1 to the 40 mL of 0.016 M sodium hydroxide solution of step 2 with stirring while continuously supplying nitrogen gas to obtain a first suspension;
step 4, transferring the first suspension to a hydrothermal synthesis reactor and then heating the first suspension at 100 degrees Celsius (° C) for 18 hours to obtain a second suspension;
step 5, centrifuging the second suspension at 20000 g for 15 min to obtain a product, washing the product twice with double-distilled water with carbon dioxide removed to obtain a gel-like material, and storing the gel-like material in a refrigerator at 4° C.; and
step 6, drying the gel-like material of step 5 in a vacuum drying oven to obtain the nano LDH; and
wherein the nano LDH is used to prepare drugs for promoting cartilage regeneration.

* * * * *

SEQUENCE LISTING

```
Sequence total quantity: 16
SEQ ID NO: 1              moltype = DNA  length = 20
FEATURE                   Location/Qualifiers
source                    1..20
                          mol_type = other DNA
                          organism = synthetic construct
SEQUENCE: 1
ctcctcacag ttgccatgta                                                    20

SEQ ID NO: 2              moltype = DNA  length = 23
FEATURE                   Location/Qualifiers
source                    1..23
                          mol_type = other DNA
                          organism = synthetic construct
SEQUENCE: 2
gttgagcaca gggtacttta ttg                                                23

SEQ ID NO: 3              moltype = DNA  length = 21
FEATURE                   Location/Qualifiers
source                    1..21
                          mol_type = other DNA
                          organism = synthetic construct
SEQUENCE: 3
acctttgggc tgccttatat t                                                  21

SEQ ID NO: 4              moltype = DNA  length = 21
FEATURE                   Location/Qualifiers
source                    1..21
                          mol_type = other DNA
                          organism = synthetic construct
```

```
SEQUENCE: 4
tccctcactc caagagaaga t                                                     21

SEQ ID NO: 5              moltype = DNA   length = 22
FEATURE                   Location/Qualifiers
source                    1..22
                          mol_type = other DNA
                          organism = synthetic construct
SEQUENCE: 5
acccaaggac tggaatcttt ac                                                    22

SEQ ID NO: 6              moltype = DNA   length = 21
FEATURE                   Location/Qualifiers
source                    1..21
                          mol_type = other DNA
                          organism = synthetic construct
SEQUENCE: 6
gccattctta tacaggccta c                                                     21

SEQ ID NO: 7              moltype = DNA   length = 21
FEATURE                   Location/Qualifiers
source                    1..21
                          mol_type = other DNA
                          organism = synthetic construct
SEQUENCE: 7
aggaggctgg cagctgtgtg c                                                     21

SEQ ID NO: 8              moltype = DNA   length = 21
FEATURE                   Location/Qualifiers
source                    1..21
                          mol_type = other DNA
                          organism = synthetic construct
SEQUENCE: 8
cactggcagt ggcgaggtca g                                                     21

SEQ ID NO: 9              moltype = DNA   length = 21
FEATURE                   Location/Qualifiers
source                    1..21
                          mol_type = other DNA
                          organism = synthetic construct
SEQUENCE: 9
aagaacgacg accaaaagga c                                                     21

SEQ ID NO: 10             moltype = DNA   length = 20
FEATURE                   Location/Qualifiers
source                    1..20
                          mol_type = other DNA
                          organism = synthetic construct
SEQUENCE: 10
catcccctat accatcgcca                                                       20

SEQ ID NO: 11             moltype = DNA   length = 21
FEATURE                   Location/Qualifiers
source                    1..21
                          mol_type = other DNA
                          organism = synthetic construct
SEQUENCE: 11
ccatgctgga tgagagaggt t                                                     21

SEQ ID NO: 12             moltype = DNA   length = 23
FEATURE                   Location/Qualifiers
source                    1..23
                          mol_type = other DNA
                          organism = synthetic construct
SEQUENCE: 12
ttggtagcag tatggatatg ggt                                                   23

SEQ ID NO: 13             moltype = DNA   length = 22
FEATURE                   Location/Qualifiers
source                    1..22
                          mol_type = other DNA
                          organism = synthetic construct
SEQUENCE: 13
cgaacactac catgatggga aa                                                    22

SEQ ID NO: 14             moltype = DNA   length = 23
FEATURE                   Location/Qualifiers
source                    1..23
                          mol_type = other DNA
```

```
                    organism = synthetic construct
SEQUENCE: 14
ttctgatgac gatggagaca cta                                          23

SEQ ID NO: 15       moltype = DNA   length = 23
FEATURE             Location/Qualifiers
source              1..23
                    mol_type = other DNA
                    organism = synthetic construct
SEQUENCE: 15
agtcctcaag cctcctgtac tca                                          23

SEQ ID NO: 16       moltype = DNA   length = 24
FEATURE             Location/Qualifiers
source              1..24
                    mol_type = other DNA
                    organism = synthetic construct
SEQUENCE: 16
gcagttgatt ctgattcacg tttc                                         24
```